(12) United States Patent
Azar

(10) Patent No.: US 11,684,795 B2
(45) Date of Patent: Jun. 27, 2023

(54) APPARATUS AND COSMETIC METHOD FOR PROVIDING COOLING TO A SKIN TISSUE TREATMENT HEAD

(71) Applicant: POLLOGEN LTD., Yokneam Ilit (IL)

(72) Inventor: Zion Azar, Shoham (IL)

(73) Assignee: POLLOGEN LTD., Tel Aviv (IL)

( * ) Notice: Subject to any disclaimer, the term of this patent is extended or adjusted under 35 U.S.C. 154(b) by 1327 days.

(21) Appl. No.: 16/125,738

(22) Filed: Sep. 9, 2018

(65) Prior Publication Data
US 2019/0001145 A1 Jan. 3, 2019

Related U.S. Application Data

(63) Continuation of application No. PCT/IB2017/051454, filed on Mar. 13, 2017.
(Continued)

(51) Int. Cl.
*A61N 5/00* (2006.01)
*A61F 7/00* (2006.01)
(Continued)

(52) U.S. Cl.
CPC ............... *A61N 5/00* (2013.01); *A61F 7/007* (2013.01); *A61H 9/0057* (2013.01); *A61N 1/403* (2013.01);
(Continued)

(58) Field of Classification Search
CPC ........ A61B 18/203; A61B 2018/00005; A61B 2018/00464; A61B 2018/00476; A61B 2018/00642; A61B 2018/00714; A61B 2018/00797; A61F 2007/0008; A61F 2007/0022; A61F 2007/0056; A61F 2007/0071; A61F 2007/0086; A61F 2007/0087; A61F 2007/0096; A61F 2007/0239; A61F 2007/0285; A61F 2007/029; A61F 7/007; A61F 7/02; A61H 2201/10; A61H 9/0057; A61N 1/06;
(Continued)

(56) References Cited

U.S. PATENT DOCUMENTS

| 5,086,786 A | 2/1992 | Sogawa et al. |
| 8,834,547 B2 | 9/2014 | Anderson et al. |

(Continued)

FOREIGN PATENT DOCUMENTS

WO 2009072108 6/2009

OTHER PUBLICATIONS

Search Report—PCT Application No. PCT/IB17/051454, dated Jun. 19, 2017, 11 pages.
(Continued)

*Primary Examiner* — Mark D Remaly
(74) *Attorney, Agent, or Firm* — ISUS Intellectual Property PLLC; Anthony Jason Mirabito

(57) ABSTRACT

A device for cooling the skin tissue of a patient during a procedure using energy includes a mat-like structure, the mat-like structure having a bottom wall, a top wall and upstanding walls connecting the top wall and the bottom wall, the walls defining an enclosed volume; it also includes one or more electrodes positioned to protrude from the bottom wall and extend through the volume for connection to a source of energy; further, the volume defines a space for holding a cooling substance for cooling the one or more electrodes and the skin tissue during an energy-based procedure.

12 Claims, 6 Drawing Sheets

Related U.S. Application Data

(60) Provisional application No. 62/308,360, filed on Mar. 15, 2016.

(51) Int. Cl.
| | |
|---|---|
| *A61H 9/00* | (2006.01) |
| *A61N 1/40* | (2006.01) |
| *A61N 7/02* | (2006.01) |
| *A61B 18/20* | (2006.01) |
| *A61B 18/00* | (2006.01) |
| *A61N 1/08* | (2006.01) |
| *A61F 7/02* | (2006.01) |
| *A61N 5/067* | (2006.01) |
| *A61N 1/06* | (2006.01) |
| *A61N 7/00* | (2006.01) |

(52) U.S. Cl.
CPC .............. *A61N 7/02* (2013.01); *A61B 18/203* (2013.01); *A61B 2018/00005* (2013.01); *A61B 2018/00464* (2013.01); *A61B 2018/00476* (2013.01); *A61B 2018/00642* (2013.01); *A61B 2018/00714* (2013.01); *A61B 2018/00797* (2013.01); *A61F 7/02* (2013.01); *A61F 2007/0008* (2013.01); *A61F 2007/0022* (2013.01); *A61F 2007/0056* (2013.01); *A61F 2007/0071* (2013.01); *A61F 2007/0086* (2013.01); *A61F 2007/0087* (2013.01); *A61F 2007/0096* (2013.01); *A61F 2007/029* (2013.01); *A61F 2007/0239* (2013.01); *A61F 2007/0285* (2013.01); *A61H 2201/10* (2013.01); *A61N 1/06* (2013.01); *A61N 1/08* (2013.01); *A61N 5/067* (2021.08); *A61N 2005/005* (2013.01); *A61N 2007/0008* (2013.01); *A61N 2007/0034* (2013.01)

(58) Field of Classification Search
CPC .... A61N 1/08; A61N 1/403; A61N 2005/005; A61N 2007/0008; A61N 2007/0034; A61N 5/00; A61N 5/067; A61N 7/02
See application file for complete search history.

(56) References Cited

U.S. PATENT DOCUMENTS

| | | |
|---|---|---|
| 2010/0049178 A1 | 2/2010 | Deem et al. |
| 2013/0178764 A1 | 7/2013 | Eckhouse et al. |
| 2014/0171934 A1 | 6/2014 | Flyash et al. |
| 2014/0276055 A1 | 9/2014 | Barthe et al. |

OTHER PUBLICATIONS

Extended European Search Report—Corresponding U.S. Appl. No. 17/765,948, dated Sep. 18, 2019, 2 pages.

APPARATUS AND COSMETIC METHOD FOR PROVIDING COOLING TO A SKIN TISSUE TREATMENT HEAD

RELATED APPLICATIONS

The present invention is a continuation application of PCT Application No. PCT/IB17/051454, filed Mar. 13, 2017, which relates to and claims priority to U.S. Provisional Application Ser. No. 62/308,360, filed Mar. 15, 2016, the entire contents of which are herein incorporated by reference.

FIELD OF THE INVENTION

The present invention relates to skin tissue treatment devices and in particular cooling devices for skin tissue treatment devices.

BACKGROUND

Presently there are a variety of energy-based tissue treatment devices in use. These include: light energy devices employing laser or IPL, RF energy devices and ultrasonic devices. All of them have in common the potential problem that at the point of contact of the device with the skin (and below the skin) a heat buildup may occur. Conventionally, cooling devices are employed which contact the skin tissue and cool the skin tissue for avoiding adverse effects such as burning, reducing pain and discomfort. These cooling devices vary in structure and operation, but may include cooling plates using Pelletier technology, cold blown air or even cold fluid filled structures placed against the skin surface. In each of these cases, relatively expensive devices are employed.

When treating the human body with such energy sources (IPL, laser, Ultrasound or RF) the temperature of selected tissues usually increases, causing cellular proteins to denature, aggregate, and lose their biological activity. This in turn leads eventually to cell necrosis. The complexity of metabolic and regulatory pathways used by living cells leads to complex mechanisms during the necrotic process as well. Some studies conclude that the lipid bilayer, and perhaps some membrane-bound ATPase enzymes are the macromolecules most likely implicated in thermal damage (Despa, F., Orgill, D. P., Neuwalder, J., Lee, R. C., "The relative thermal stability of tissue macromolecules and cellular structure in burn injury," Burns 31(5), 568-577 (2005)).

In general, it is the combination of temperature levels and the exposure time to elevated temperatures that induces necrotic processes in living cells. One can use the term accumulated thermal dose to describe this combination. Several studies indicate that there is a correlation between cell death and the rate of delivery of accumulated thermal dose during photothermal exposure (Michael L. Denton; Gary D. Noojin; B. Giovanna Gamboa; Elharith M. Ahmed; Benjamin A. Rockwell, "Photothermal damage is correlated to the delivery rate of time-integrated temperature", SPIE 9706, Optical Interactions with Tissue and Cells XXVII, 97061M (7 Mar. 2016)).

When targeting specific organ (e.g. sweat glands, sebaceous glands, hair follicles, fat cells . . . ), the objective is to induce necrotic process only in the targeted organ, while leaving the surrounding tissue intact, namely, increasing the target organ temperature to levels where necrotic processes are initiated while maintaining the surrounding tissue temperature at safe levels. There are several approaches one can take to accomplish that.

One approach is to utilize differences in absorption spectra and then to apply energy at specific wave band(s) that are better absorbed by the targeted organ than its surrounding tissue.

Inducing the desired temperature difference can also be obtained by using the energy source in a pulsed mode. When designed properly, differences in thermal relaxation times cause the target tissue to maintain its elevated temperature for longer time, increasing the probability of necrotic and apoptotic processes to occur in it. In most such cases, this kind of treatment is accompanied with the application of local cooling of the area of the skin tissue which is treated. This method, although considered effective for many skin types, is usually not considered safe for treating people with dark skin and as it might produce severe burns.

Bulk heating can also be utilized in some cases. As mentioned above, necrotic and apoptotic processes are complex and different organs will require different temperature levels to initiate them. If a necrotic or apoptotic process occurs in a specific organ at lower temperature than in the surrounding tissue, heating the tissue bulk to that temperature for long enough will eventually induce necrotic process to the target organs with minimal effect on the surrounding tissue. Studies have shown that extended exposure to a temperature of around 45° C. generates destruction of hair follicles (F. Urdiales Gálvez, M. Al-Zaruni, M. A. Trelles, "SHR— New Offer in Photo-Epilation", www.almalasers.nl/downloads/soprano/sbr_new_offer.pdf).

A typical laser system which may be used for bulk heating is one which emits a continuous pulse sequence (such as, for example, 10 Hz 20 ms); the clinician glides the treatment head over an extended treated area, causing a gradual temperature increase in this area by repeated "visits" at the same spots. For example, when treating a 100 cm² area, six to ten multiple passes are required (Braun, Martin. "Permanent laser hair removal with low fluence high repetition rate versus high fluence low repetition rate 810 nm diode laser—a split leg comparison study." J Drugs Dermatol. 8.11 Suppl (2009): S14-17.), and the entire treatment may take about 15-20 minutes. Larger treatment areas may require significantly longer times. The continuous movement of the handpiece over the skin surface while delivering laser pulses, is essential to prevent energy from concentrating on a particular area on the skin tissue surface which might result in burns due to overheating.

This method of bulk heating is typically applied without any epidermal cooling. Although safer than the high fluence pulse method discussed previously when treating dark skin, it is considered less effective, especially when treating light hair or when trying to treat specific glands.

SUMMARY OF THE PRESENT INVENTION

The present invention provides two general embodiments. The first embodiment includes a receptacle in the form of a box which is hollow to receive a source of a coolant material as well as one or more electrodes that pass through the box and are upstanding on the bottom surface of the box to contact the skin surface. In this arrangement, the electrodes are cooled so that the skin tissue surface contacted will remain cool even after the electrodes pass energy, such as RF energy, through the electrodes. This first embodiment also may include one or more holding straps which hold the treatment device onto the skin tissue surface while being treated. The electrodes in the box are attached to a source of RF energy and a controller.

In particular, and in an aspect, a device for cooling the tissue of a patient, the device includes: a container-like structure, the container-like structure having a solid bottom wall, one or more upstanding side walls and top wall. The solid bottom wall and the one or more upstanding side walls defining a volume. One or more electrodes are formed in the solid bottom wall; the volume defines a space for holding a cooling substance for cooling the one or more electrodes.

In another aspect, the electrodes may include electrical connections adapted to be connected to a source of electromagnetic energy. The source of energy may be one of RF or ultrasound energy. The cooling substance may be ice or a gel-like material.

In a further aspect, the device may have a removable top wall for receiving the ice or a cooling substance and may further include a securing belt to secure the device to a patient. The device may be in the form of a container-like structure whose shape is one of: rectangular, square, circular or an oval shape.

In another aspect, a method of cooling a patient's tissue during treatment using the device described may include: placing a cooling substance within the container-like structure; placing the container-like device on the tissue surface of the patient with the one or more electrodes being in contact with the tissue surface; activating the source of electromagnetic energy to the one or more electrodes. Thus, the one or more electrodes are cooled by the cooling substance. A further step may include replacing the cooling substance once it has been depleted with a new cooling substance. The cooling substance may be ice.

In another aspect, a device for cooling the skin tissue of a patient during a procedure using energy includes: a mat-like structure, the mat-like structure having a bottom wall, a top wall and upstanding walls connecting the top wall and the bottom wall, the walls defining an enclosed volume; also it includes one or more electrodes positioned to protrude from the bottom wall and extend through the volume for connection to a source of energy; the volume provides a space for holding a cooling substance for cooling the one or more electrodes and the skin tissue during an energy-based procedure. The source of energy may one or more of RF or ultrasonic energy. Further, the enclosed volume may be divided into a plurality of cells, each of the cells containing one or more of the electrodes.

In a further aspect, the device of further includes a coolant temperature sensor in one or more of the cells, the one or more temperature sensors sensing the temperature of the cooling substance. The one or more coolant temperature sensors may be connected to a programmed controller, the programmed controller being enabled to receive and display the sensed temperature of the cooling substance. Further, the one or more electrodes may be connected to a programmed controller, the programmed controller controlling the application of energy to the one or more electrodes.

In yet a further aspect, the device may include or more skin tissue temperature sensors on the bottom wall, the one or more temperature sensors measuring the skin tissue temperature of the patient. The one or more skin tissue temperature sensors may be connected to a programmed controller, the programmed controller being controlled to receive the patient skin temperature from the one or more skin temperature sensors and control the amount of EM energy imparted to the one or more electrodes.

In another aspect, the mat-like structure may be made of a flexible material to allow conformity of the mat-like structure to the skin tissue when in contact with the skin tissue. Further, a vacuum source may be connected to the mat-like structure, wherein activation of the vacuum source draws the mat-like structure into contact with the patient skin tissue. The one or more electrodes may be a plurality of electrodes formed into an X-Y matrix, and wherein the electrodes may be operatively connected to a programmed controller and wherein the programmed controller is operated to selectively apply a signal to activate one or more of the plurality of electrodes. The programmed controller may selectively apply a signal to two or more electrodes having a distance A or a distance B greater than A between the two or more electrodes, the distance A being selected for a shallower treatment such as hair removal and the distance B for targeting deeper tissue such as in fat cells.

In a further aspect, the programmed controller may be operative to select any two or more electrodes in the X-Y array to effect one or more of: hair removal or fat cell destruction. The programmed controller may be operative to select all of the electrodes for bulk heating of the skin tissue.

In yet another aspect, a cosmetic method of skin treatment for one or more of hair removal or fat cell reduction, includes the steps of: providing the above-described device; selecting one or more of hair removal or fat cell reduction to be programmed into the programmed controller; and activating selected electrodes in the X-Y matrix of electrodes to effect one or more of hair removal or fat cell reduction. The method may include the step of selecting all the electrodes in the X-Y matrix for bulk heating. The method may also include the step of cooling the skin tissue before, during and/or after activating the electrodes.

In a yet further aspect, the cosmetic method may include the step of applying a vacuum source to draw the mat-like structure into contact with the skin tissue during the activation of the selected electrodes, as well as the step of applying a gel to the skin tissue to improve thermal contact, electrical contact and cooling of the skin tissue.

In yet another aspect, the device may further include a source to pulsate the vacuum source so as to provide a massaging action to the skin tissue as well as the step of pulsating the application of the vacuum source to provide massaging of the skin tissue. In the device, the vacuum source may draw the mat-like structure into contact with the patient skin tissue through one or more passages formed in the mat-like structure. The gel may be applied to the skin tissue through passages formed in the device.

While the above first embodiment may be simple in structure and operation, a second embodiment has been developed that incorporates some aspects of the first embodiment with further features. Whereas with the first embodiment described above and further herein is simple, it has limitations, such as the size of the container-like structure that may be placed on a patient's skin and fully contact the skin throughout the bottom surface of the structure due, for example, the stiffness of the container material not conforming to the natural curves of a patient's body. Further, the use of straps to hold the container on the patient's body surface may be not only inconvenient but also uncomfortable.

A more convenient solution while maintaining the essentials of the first embodiment, such as cooled electrodes that contact the body, may be found in the second embodiment herein. The second embodiment includes a cooling substance interfaced in an array of electrodes in a mat form which may be formed of a material which is flexible and conforms to the patient's body curves, allowing for a hand-free treatment. The array of cooling materials with electrodes on the mat may be made in any suitable shape and size and may even be formed into tubular-like structures in order to, for example, surround a patient's limb to be treated.

Depending on the number and orientation of the electrodes in the mat as well as the energy-activating agent (such as RF or ultrasound), as well as the amount of time activated either continuously or in pulses, the device when activated may be used to reduce/remove hair and/or reduce the number of fat cells. Since the depth of the fat cells below the tissue surface in a "typical" body is different from the depth of hair follicles below the tissue surface, this difference provides the ability to adjust the penetration depth of the activating energy source to either reduce fat or reduce/remove hair or both, as will be detailed in the following discussion.

DETAILED DESCRIPTION OF THE PRESENT INVENTION

The present invention in a sense "breaks the mold" and provides cooling of skin tissue using a simple, non-mechanical, non-electric device.

The First Embodiment of the Present Invention

In the first embodiment, the device provides a receptacle that may be filled with water or another liquid or solid material and frozen in a common freezer. The device also includes, by way of example only, RF electrodes which are placed in contact with the patient's skin. Since, in the context of a RF skin treatment device, heat is generated under the skin and on the skin surface, the hottest points are at the point of contact of the RF electrodes with the skin tissue, and thus it may be useful to provide cooling at the electrodes themselves.

Figure 1:
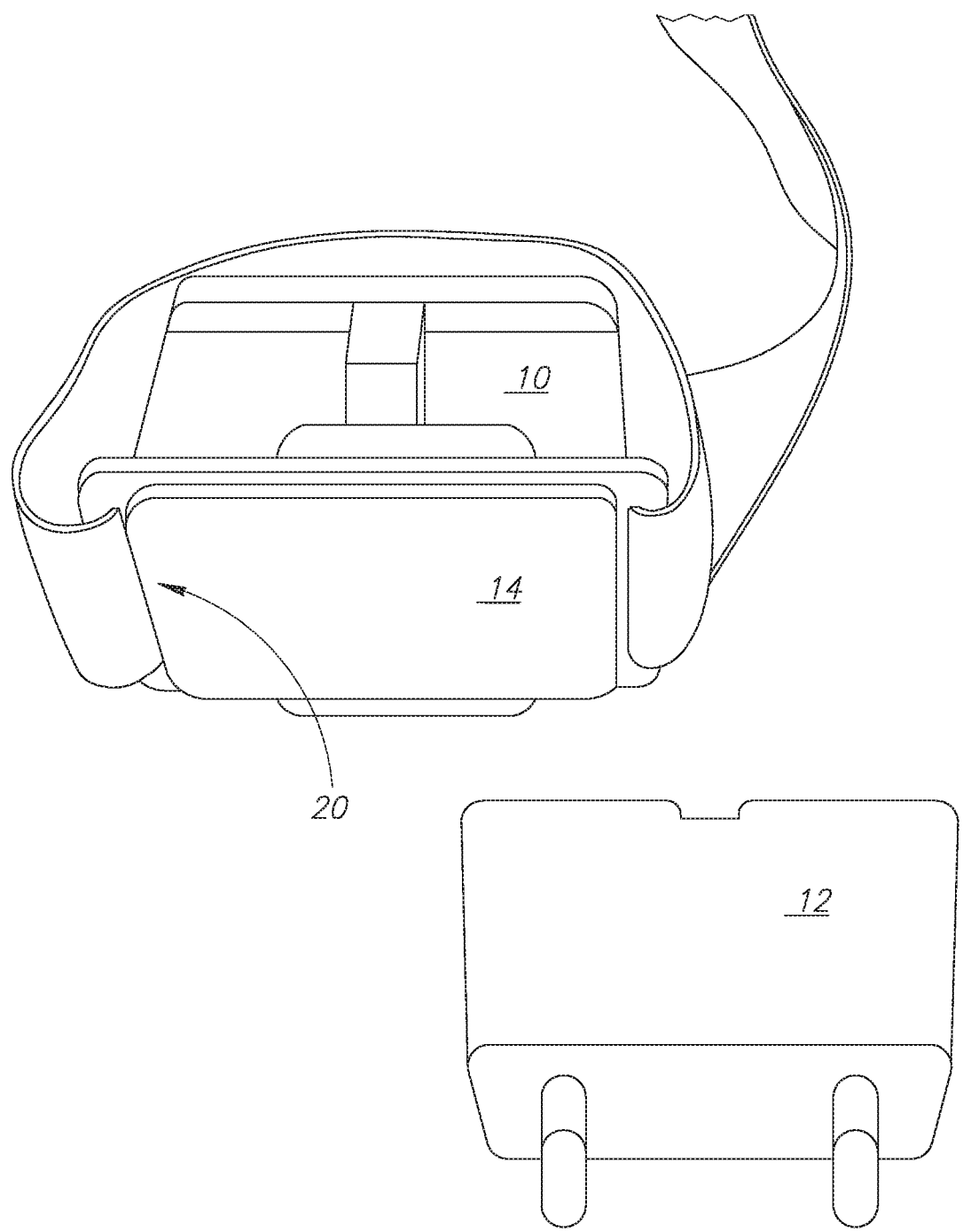
FIG. 1 is a multiple perspective view of the apparatus of the first embodiment of the present invention.
Figure 2:
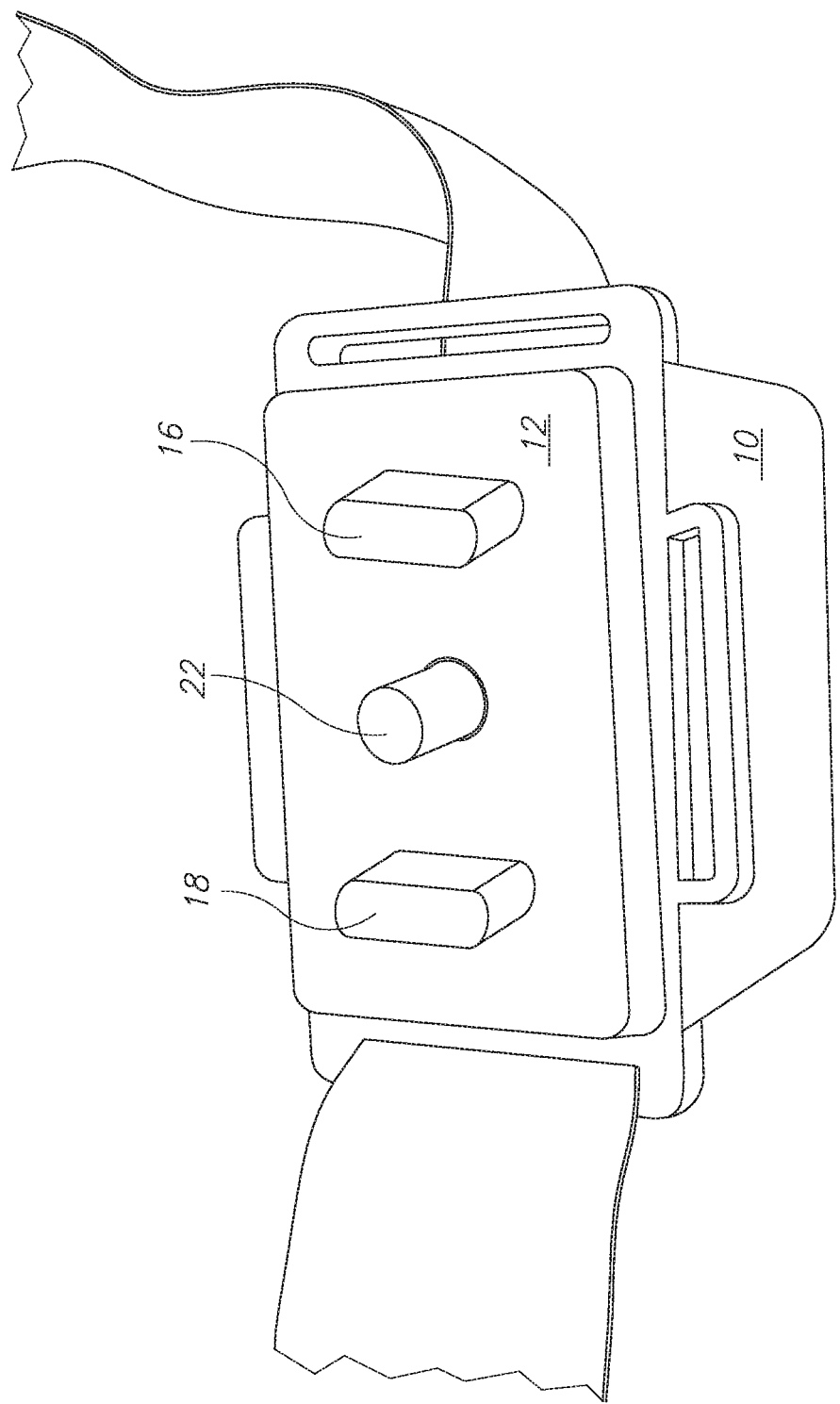
FIG. 2 is a bottom view of the apparatus of the first embodiment of the present invention.
Figure 3:
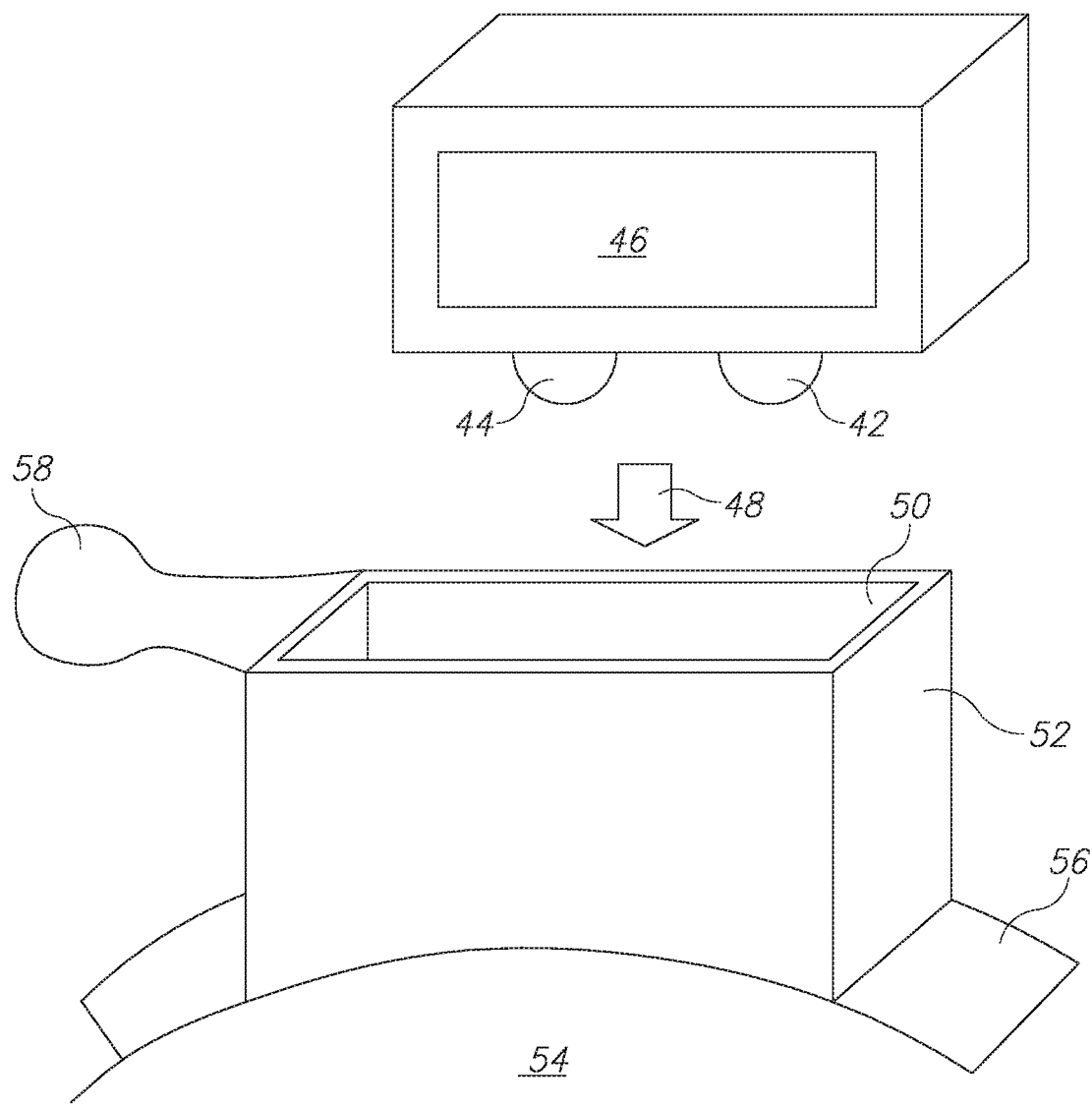
FIG. 3 is view of the apparatus of the first embodiment of the present invention and a receptacle for receiving the apparatus.

Attention is directed to FIGS. 1-3 of the accompanying drawings. Turning first to FIG. 1, this figure illustrates the RF treatment head which is shown as having two components 10 and 12. Component 10 is a holder with an opening enclosing a volume 14. Volume 14 may be filled wholly or partially with a liquid or solid material, which, as mentioned above, may be placed in a freezer and frozen fully or partially. Component 12 is sized to fit inside the component 10 and within the volume 14. Component 12 enclosing internal volume which may also be filled wholly or partially with the cooling material. Protrusions 16 and 18 are representations of electrodes, in this case RF electrodes, although in use the electrodes are likely to be metal or at least metal coated. Also, electrical connections to the electrodes are not shown in the figures herein. A web or strap 20 may be employed to attach the treatment head onto a body part such as an arm, a leg or the abdomen.

FIG. 2 shows the components 10 and 12 when assembled together in a "use" configuration. An additional electrode/sensor 22 may be provided to measure the temperature or other physical characteristics of the skin surface and to provide feedback to a programmed controller to modify treatments provided to the patient. Further, an additional sensor (not shown) may sense the temperature of the coolant within the components 12 or 10 so that it may be replaced when it no longer is sufficient to cool the skin tissue. A belt 23 shown in FIG. 2 may be used to secure the apparatus 10 onto a body portion such as the torso or a limb. The belt 23 may be threaded through loops 25 and 27 formed on the apparatus 10.

It is to be understood that while the above device has been described in terms of a RF treatment head, any other type treatment head may be employed, such as an ultrasound head having electrodes or even a laser treatment head in which the apparatus of the present invention may be placed directly on the skin surface and an aperture provided through the device to allow the laser energy to pass through the device and to the skin surface. Also, it is to be understood that while the shape of the treatment head is shown to be generally rectangular, it may be square, round, oval or any suitable shape adapted for placement on the skin of the patient. The material in the device may be water which can be cooled or frozen to form ice, or any other coolant fluid/gel-type material such as that used in "ice packs" that may be placed in the freezer and cooled down or even dry ice in pellet or solid form.

Once the material in the device of the present invention has lost it cooling ability through heat transfer, it can simply be put back into the freezer to refreeze the contents. Any number of these units may be kept in the freezer and pulled out when needed.

In a variation of the first embodiment described herein embodiment, the device may be modular in which the cooling substance and the electrodes with connections are in a first unit and a second unit is a handpiece into which the first unit fits. This allows for the second unit to be placed on the patient's skin and even secured thereto, and for the first unit to be dropped into and replaced when the cooling substances has been depleted. A simple schematic implementation of this embodiment is illustrated in FIG. 3 in which the first unit with electrodes 42 and 44 having an internal cooling substance 46 may be inserted in the direction of arrow 48 into the interior 50 of the second unit handpiece 52 which may be secured to the patient's body portion 54 by a belt 56. A handle 58 may also be provided if the second unit is desired to be moved about on the body portion 54 instead of being belted down.

The Second Embodiment of the Present Invention

The second embodiment of the present invention provides an alternative solution to the first embodiment by providing bulk heating using RF energy in connection with a cooling surface material to be described below.

Figure 4A:
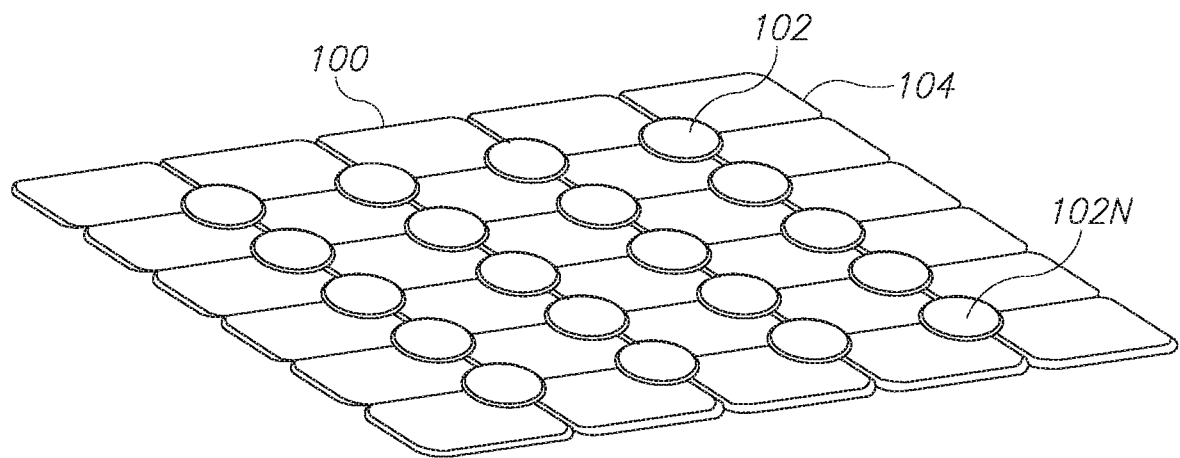
FIGS. 4A and 4B are perspective views of alternative devices in accordance with the second embodiment of the present invention.
Figure 4B:
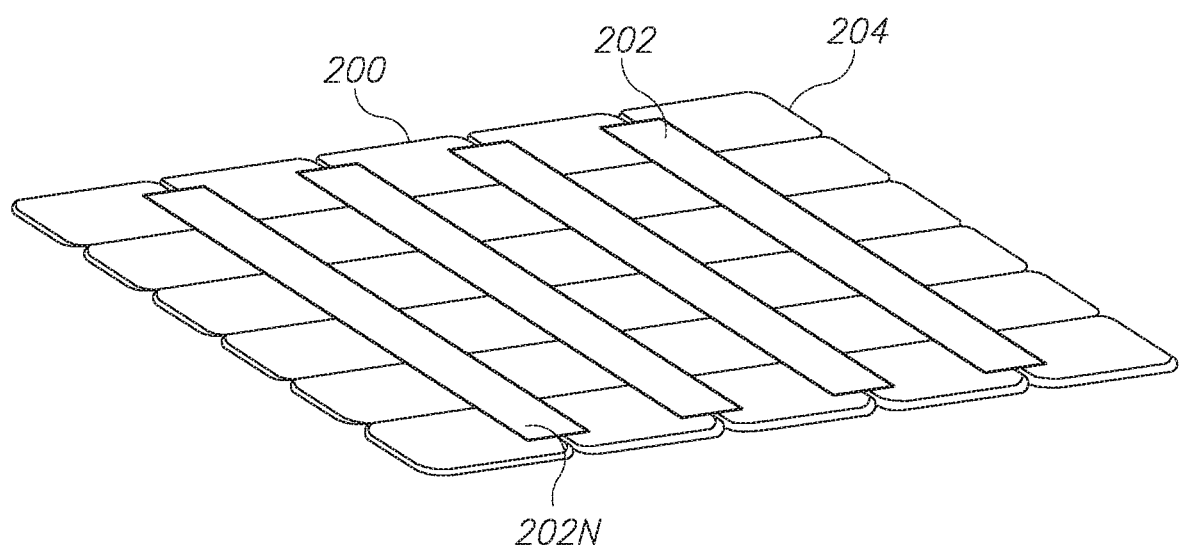

FIGS. 4A and 4B illustrate a number of optional arrays of mats of electrodes which may be used for such bulk heating treatments. One can consider using rectangular arrays (FIG. 4A), triangular, hexagonal or an array of linear elongated electrodes (FIG. 4B), or any other geometrical configuration that is suitable for treatment purposes. As may be seen in FIGS. 4A and 4B, the mats 100 and 200 therein may include electrodes 102 . . . 102n and 202 . . . 202n. As many or as few as desired may be mounted into mats 100 and 200. In addition, the electrodes are mounted within cooling packs 104 and 204. It is to be understood that the cooling packs may be similar in form to commercial cooling mats that are used commercially to cool items, modified, of course, to add one or more electrode pairs. It is also to be understood that the views provided in FIGS. 4A and 4B are "bottom-side" views and that it is this side of the mats that are placed in contact with the skin tissue to be treated. Due to the "segmented" nature of the individual cooling pack cells 106 and 206, the mats may be overall "floppy" so that when placed on a body, the mats will conform to the body curves and be in good contact with the skin tissue.

Electrode spacing will determine the penetration depth. When treating a patient for hair removal, the aim is to increase the temperature of the dermis, and subcutaneous layer in the depth range between 2 mm to 4 mm, to a temperature level of at least 45° C., and keep it at that temperature level for an extended period of time (~20 minutes). It is preferred that temperature levels in other regions in the treated zone are kept at lower levels to avoid undesired effects and to provide a gentler treatment to the patient. A suitable RF pulse activation protocol is key in generating and maintaining the desired temperature distribution in the skin treated zone. The desired RF delivery profile is pulsed delivery which provides enough time for superficial layers to stay cool by both direct external cooling and natural skin cooling mechanisms.

To enhance treatment safety one can consider adding a cooling mechanism to the skin surface of the treated area. There are several options with which to accomplish that goal and depending on the treated area and the patient, the clinician might select to implement various methods. One approach may implement the use of a cold pack or cooling sheet which consists of individual pockets which are filled with coolant, forming sort of a continuous sheet. Generally, cooling sheets containing a plurality of individual cells continuing water or another fluid are known for cooling food or person. One such cooling mat is the Thermos® 9 Cube Ice mat. Another is Cryopak Flexible Ice Pack and yet another is the Uline Ice Blanket, all of which are commercially available the electrodes may be embedded between these pockets and have good thermal contact with them while maintaining electrical insulation (see FIGS. 4A and 4B). Made of a flexible material, such a segmented sheet may comprise individual pockets to maintain its flexibility throughout the treatment as well as conform itself to the patient's skin tissue contours. The cooling sheet can be a closed container that maintains the coolant encapsulated inside. In this case, the cooling pack is cooled, as discussed above in connection with the first embodiment of the present invention, before the treatment by keeping it in a refrigerator or freezer at a desired temperature.

Another approach may implement a cool pack or cool sheet which is connected to an external cooling system through tubes or even implement cooling through a TEC. Proper design of the coolant channels in the cooling pack and maintenance of a low enough internal pressure will guarantee the maintenance of flexibility of the cooling pack.

Figure 5A:
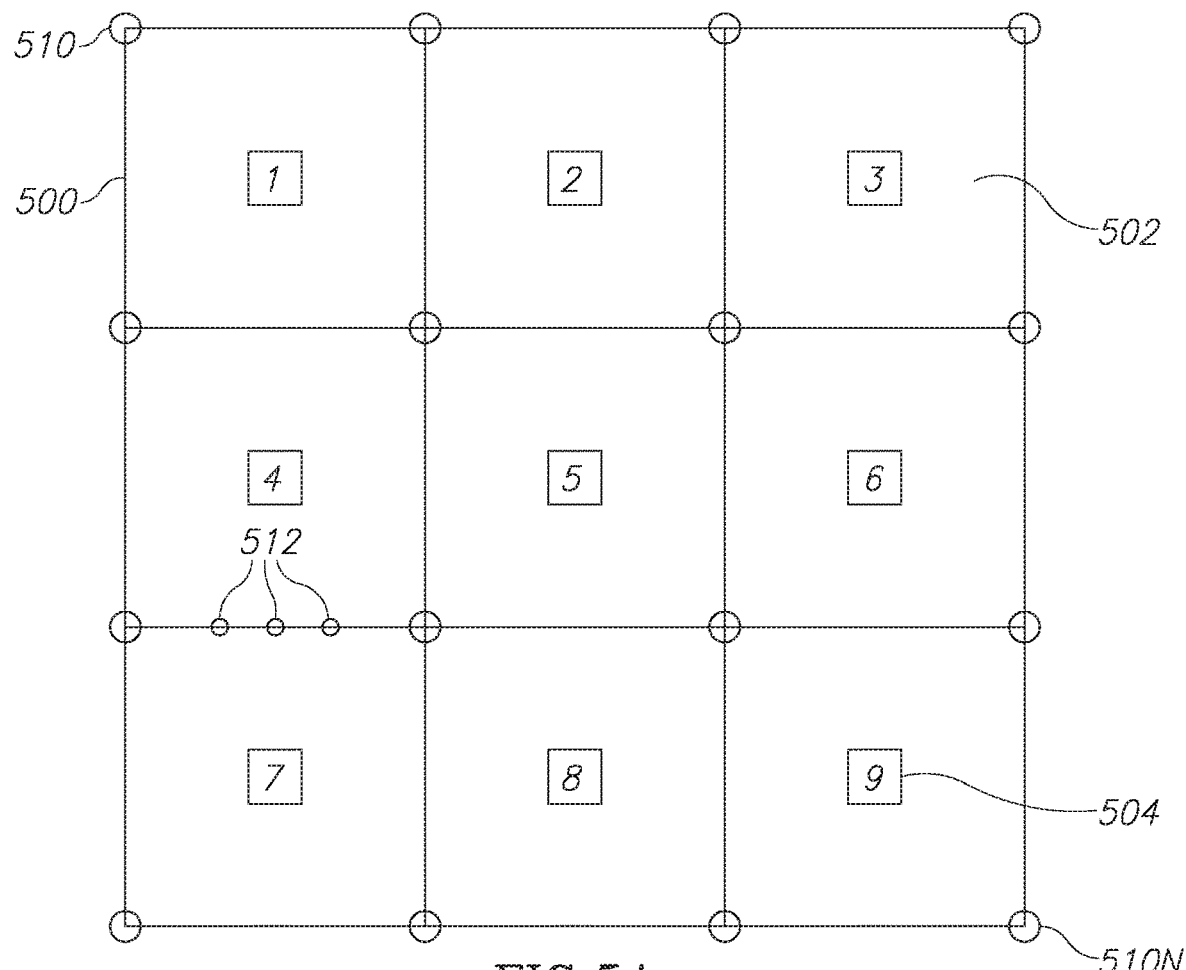
FIGS. 5A and 5B are bottom and side views of another alternative device of the second embodiment of the present invention.
Figure 5B:
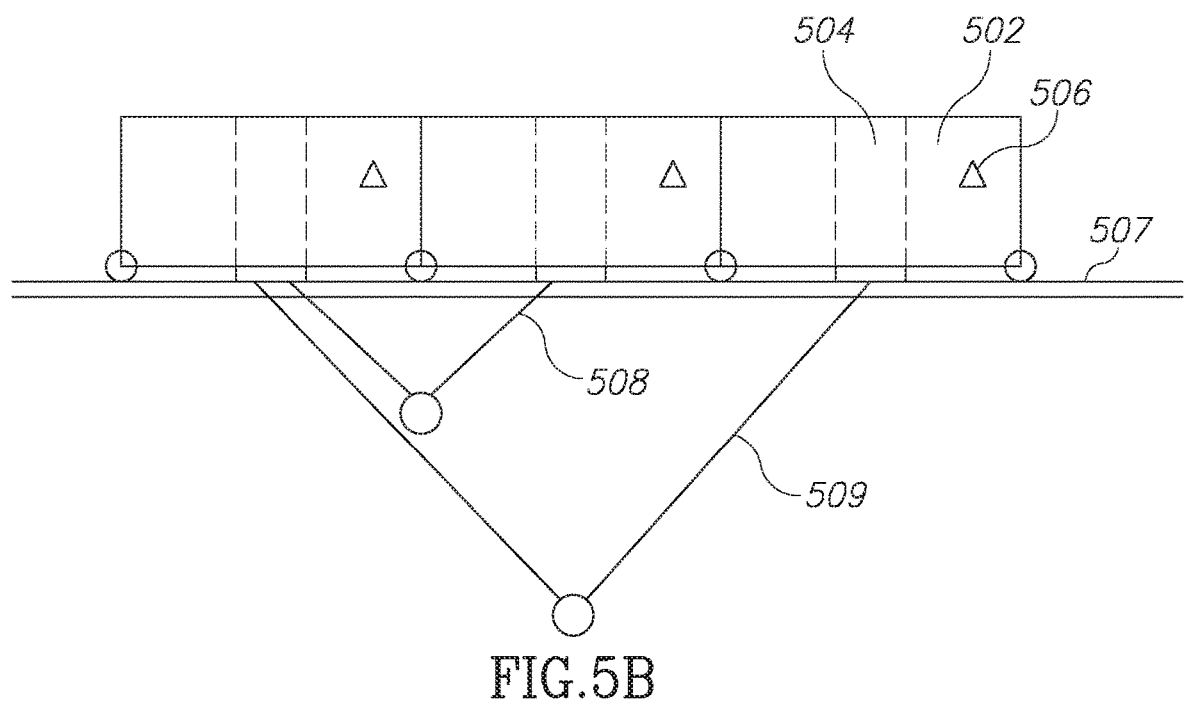

FIGS. 5A and 5B illustrate another variation of the second embodiment. A mat 500 is shown in bottom (FIG. 5A) and side (FIG. 5B) views. The mat 500 may include an X by Y matrix of cells 502 (which may be of any size and number desired), each of which may include an electrode 504 and a temperature sensor 506 within each cell to measure and then indicate to an operator the temperature of the liquid or other type coolant within the cell. As seen in FIG. 5B, the electrode 504 is contained in or immersed in a cell in order for the electrode to be cooled at the portion on the bottom in which it contacts the skin tissue, although optionally the electrode could be placed at the interstices of the cells.

Further, FIG. 5B illustrates one aspect of the operation of the present invention. In that figure, reference numeral 507 refers to the surface of the skin tissue. When adjacent pairs of electrodes are activated, the pairs result in treatment at a depth illustrated by reference numeral 508, the depth of hair follicles to be treated/destroyed. However, when more distance exists between activated electrodes, the depth of treatment may be, as shown in connection with the reference numeral 509, in the area of fat cells to be reduced/destroyed. Of course, the present invention also envisions the ability to select adjacent (nearest neighbor) and not so adjacent electrodes (next nearest neighbor or beyond) systematically or even randomly to achieve desired results, or even activating all the electrodes for bulk heating.

The cells may be electrically isolated from one another to prevent developing short circuits between adjacent cells. In addition, a number of skin temperature sensors 510 . . . 510n are shown as being at the interstices of the cells. These skin temperature sensors may measure skin temperature across and throughout the mat 500. It is to be understood that the skin temperature sensors, the coolant temperature sensors 506 and the electrodes are connected to a source of electrical power and preferably to a programmed controller which monitors the coolant temperature sensors 506 and the skin temperature sensors 510 and controls activation of the electrodes 504. A user interface may provide controls for the operator as well as a display screen to display various parameters in the operation of the device.

The coolant temperature sensors 506 will indicate which cells have lost their cooling capacity due to RF energy passing through the electrodes and signal to the operator on the user interface to replace the mat. If the cooling material is active, like cooled passages to an outside refrigerator unit or to a TEC device, the sensors may signal the cooling units to be activated and re-cool the fluid in the cells. While fluid may be used as a cooling medium, it is envisioned that a solid or gel or other material (including a TEC) may be used. While it is envisioned that the mat may be made of flexible materials, harder materials may be used. The bottom portion of the mat may be made of a material to promote good thermal conductivity to the skin tissue and the material on the upper portion of the mat of a good thermal insulating material to maintain the temperature within the cells.

The skin temperature sensors may measure the skin temperature through their contact with the skin tissue and the treatment modified if those sensors indicate excessive heat buildup across the skin tissue under the mat or just in certain places under the mat.

It is envisioned that in operation the programmed controller will cause the RF energy to pass through the electrodes numbered 1 through 9 and heat up the skin tissue until it reaches the desired temperature range (depending on the type of treatment) and then work on an intermittent basis to maintain that level of temperature. If the temperature rises too high or drops too low, one or more of the electrodes can be re-activated to bring the skin tissue back up to the desired temperature.

In order for the mat of FIG. 5A or those of FIGS. 4A and 4B to be mounted for operation in a vacuum device such as the vacuum device of FIG. 6, to be discussed below, a number of passages 512 as shown in FIG. 5A may be formed in the mat and pass from the top side to the bottom side so that a vacuum drawn will "snug" the skin to the electrodes so that they perform their function efficiently.

The mat of FIG. 5A is shown with 9 cells (but only for purposes of illustration as any number may be accommodated). They are marked as electrodes 1 through 9. It is known that with RF energy, and here the RF energy passes through the electrodes 504 to the skin tissue, that the closer the pair of electrodes in location (assuming a bipolar arrangement), the shallower the depth of penetration of the RF energy into the skin tissue. Thus, the depth of penetration of RF energy when electrodes numbered 1 and 2 are activated will likely be less than the penetration when electrodes numbered 1 and 3 are activated. The programmed controller may be electrically connected to the electrodes numbered 1 through 9 and thus a custom program of treatment may be accomplished. For example, for hair removal closer electrodes may be activated since the hair follicles are generally situated at shallower depths that fat cells which may militate activating more distant electrodes (like 1 and 3 in the example). Obviously, many variations of parings may be made for a suitable treatment regimen, including, for example, destruction of sweat glands.

In addition to cooling, vacuum may be implemented in connection with the cold pack or cooling sheet. The vacuum can be generated through the electrodes (with proper electrode design) or through dedicated suction buttons or passages between the electrodes (like an octopus). The vacuum will improve the electrical contact of the electrodes to the skin, fix the cooling pack on the desired treatment zone and may even be used in a pulsatile mode to provide a mechanical massage effect to the skin. In addition to providing massaging by pulsing the vacuum source, a mechanical/electrical device may be provided to generate massaging of the skin tissue. This massaging may have the benefit, when the device is activated in a fat reduction mode (or otherwise) of "evening out" or leveling the tissue during and after fat cell reduction as well as in promoting the drainage of liquefied fat into the body's lymphatic system.

Figure 6:
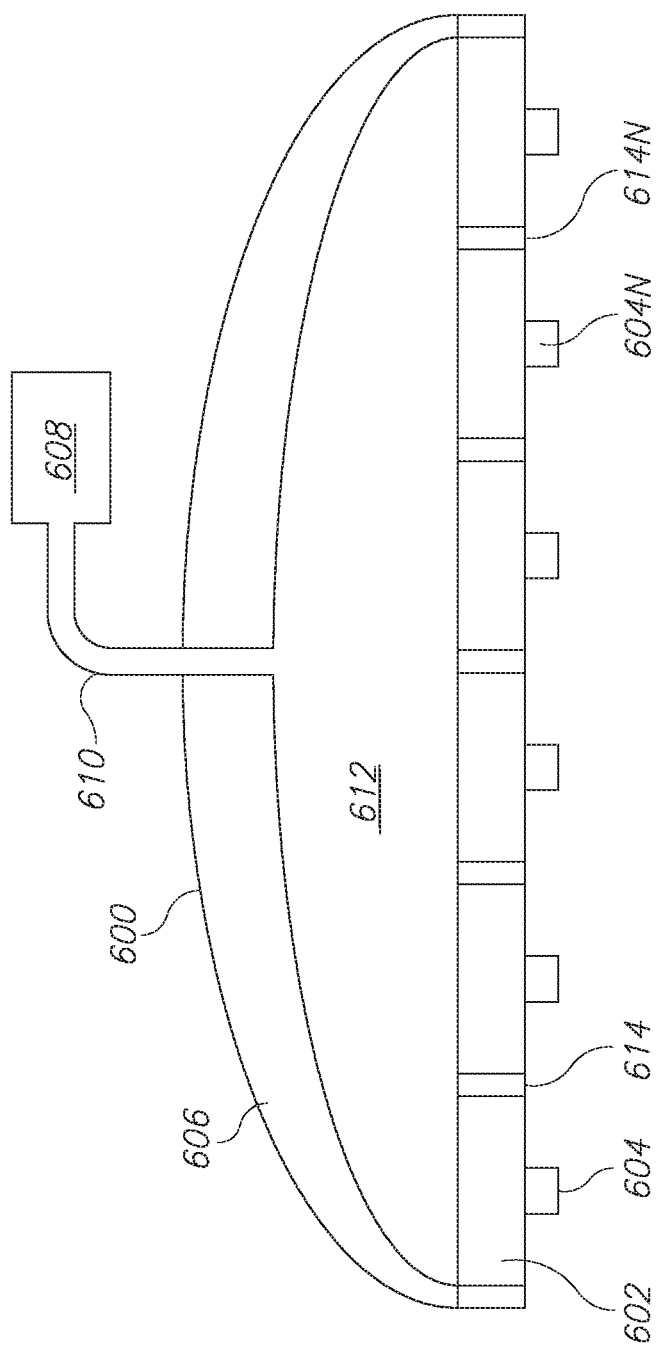
FIG. 6 illustrates an apparatus for containing the apparatus of the second embodiments of the present invention.

Another way to provide a vacuum "fit" onto the skin tissue surface is to mount the cooling mat with electrodes in a cupped frame structure such as shown in FIG. 6. In this figure, the source of vacuum may be located behind the mat which may be position and stretched across the mouth of the frame structure. Shown in FIG. 6 is a device 600 which mounts a mat 602 similar to those shown in FIGS. 4A, 4B and 5, and having electrodes 604 to 604n on the bottom surface of the mat 602 as described above. The device includes a dome-like structure 606 within the open mouth of which the mat 602 is attached by any suitable known way. In addition, a vacuum source 608 is attached through pipe or other hollow conduit 610 to the interior 612 of the apparatus 600, so that when a vacuum is drawn through passages 614 through 614n (similar to those shown in FIG. 5A as passages 512), the mat contacts the skin tissue and draws it into close contact with the mat and its electrodes. The device 600 may also contain electrical and other connections to the electrodes and various sensors, as described herein in reference to FIGS. 4A, 4B and 5.

Spreading of electrical contact enhancing gel or fluid from suitable passages in the cold pack or from the electrodes may further improve the electrical contact between the electrodes and the skin. Supply of the gel may be manual or may be by, for example, passing the gel to the skin tissue through passages 512 in FIG. 5A or 614 in FIG. 6. Electrically insulating thermal contact gel in the area between the electrodes will improve the thermal contact in that region and guarantee proper cooling of the skin epidermal layer in the entire treatment zone.

There are several advantages of using such cold packs or cooling sheets arrays for the purposes of hair removal:
1. Hands-free solution: when applying bulk heating for hair removal prior to the present invention, the clinician was required to glide the laser head over the treatment zone during the entire procedure. Depending on the size of the treatment zone, this can take a significant amount of time (sometimes more than an hour), an exhausting experience for the clinician. With the present invention, the clinician selects an electrode array configuration appropriate to the treated zone and places the chosen array on the skin. At that point, a programmed controller associated with the cold pack or cooling sheet runs the treatment procedure for a predetermined period of time. The clinician just needs to monitor the process every occasionally, allowing him/her to treat several patients in parallel.
2. Shorter treatment time for large areas: It takes about 15-20 minutes to treat an area 100 $cm^2$ in size. When treating areas larger than that, the clinician may be required work in sectors, one sector at a time, in order to maintain the proper treatment temperature levels within the treated sector (at least 45° C.). Thus, treating a large area such as the back can take more than an hour and is usually handled over several treatment sessions. With the solution of the present invention, using a large electrode array, one can treat the various sectors of a large treatment zone in parallel, reducing the overall treatment time to about 20 minutes.
3. Color blind treatment: It is well known that using laser energy to treat skin of color is not simple and might cause adverse effects such as burns. RF energy is "color blind" and treating patients of light or dark skin and light or dark hair is done with the same treatment protocols.

What I claim is:

1. A device for treating the skin tissue of a patient during a procedure using electro-magnetic (EM) energy comprising:
a mat-like structure having a bottom wall, a top wall and upstanding walls connecting the top wall and the bottom wall, the walls defining an enclosed volume, the mat-like structure being divided into a plurality of cells formed into an X-Y geometrical matrix, each of the cells containing an electrode to thereby provide a plurality of electrodes in the mat-like structure;
wherein each of the plurality of electrodes in the mat-like structure are operatively connected to a programmed controller and wherein the programmed controller is configured to selectively apply a signal from a source of EM energy to activate one or more of the plurality of electrodes;
wherein the mat-like structure is of a flexible material to allow conformity of the mat-like structure to the patient's body curves when the mat-like structure is in contact with the skin tissue.

2. The device of claim 1, wherein the source of EM energy is RF energy.

3. The device of claim 1, further comprising a coolant and a coolant temperature sensor in one or more of the plurality of cells, the one or more temperature sensors sensing the temperature of the coolant.

4. The device of claim 3, wherein the one or more coolant temperature sensors are connected to the programmed controller, the programmed controller being enabled to receive and display the sensed temperature of the coolant.

5. The device of claim 1, further comprising one or more skin tissue temperature sensors on the bottom wall, the one or more temperature sensors measuring the skin tissue temperature of the patient.

6. The device of claim 5, wherein the one or more skin tissue temperature sensors are connected to the programmed controller, the programmed controller being controlled to receive the patient skin temperature from the one or more skin temperature sensors and control the amount of EM energy imparted to the one or more electrodes.

7. The device of claim 1, further comprising a vacuum source connected to the mat-like structure, wherein activation of the vacuum source draws the mat-like structure into contact with the patient skin tissue.

8. The device of claim 1, wherein the programmed controller is configured to selectively apply a signal to two electrodes located in different cells in the X-Y geometrical matrix having a distance A or a distance B greater than A between the two electrodes, the distance A being selected for targeting shallower tissue and the distance B for targeting deeper tissue.

9. The device of claim 1, wherein the programmed controller is configured to select activation of all of the electrodes for bulk heating of the skin tissue.

10. The device of claim 7, further comprising a source to pulsate the vacuum source so as to provide a massaging action to the skin tissue.

11. The device of claim 7, wherein the vacuum source draws the mat-like structure into contact with the patient skin tissue through one or more passages formed in the mat-like structure.

12. The device of claim 1, wherein the X-Y geometrical matrix is formed into one of: a rectangular array, a hexagonal array, a triangular array, or an array of elongated electrodes.

* * * * *